United States Patent [19]
Askill et al.

[11] Patent Number: 6,001,345
[45] Date of Patent: *Dec. 14, 1999

[54] APPLICATION OF CYANOACRYLATE/ANTI-MICROBIAL COMPOSITIONS TO THE PERI-WOUND OR PERI-MUCOSAL AREA

[75] Inventors: Ian N. Askill; Michael M. Byram, both of Colorado Springs, Colo.; Richard J. Greff, St. Pete Beach, Fla.

[73] Assignee: MedLogic Global Corporation, Colorado Springs, Colo.

[*] Notice: This patent is subject to a terminal disclaimer.

[21] Appl. No.: 08/963,180

[22] Filed: Nov. 3, 1997

[51] Int. Cl.⁶ .......................... A61K 31/79; A61K 31/74; A61K 31/785; A61K 31/765
[52] U.S. Cl. ..................... 424/78.25; 424/78.31; 424/78.32; 424/78.36
[58] Field of Search ............... 424/78.25, 78.32, 424/78.31, 78.36

[56] References Cited

U.S. PATENT DOCUMENTS

| | | | |
|---|---|---|---|
| 2,784,127 | 3/1957 | Joyner et al. ........................... 154/43 |
| 3,527,224 | 9/1970 | Rabinowitz ........................... 128/334 |
| 3,591,676 | 7/1971 | Hawkins et al. ........................ 424/81 |
| 3,654,239 | 4/1972 | McIntire et al. .................... 260/78.4 N |
| 3,667,472 | 6/1972 | Halpern ............................ 128/334 R |
| 3,722,599 | 3/1973 | Robertson ......................... 128/334 R |
| 3,995,641 | 12/1976 | Kronenthal et al. .................... 128/335 |
| 4,035,334 | 7/1977 | Davydov et al. .................... 260/42.21 |
| 4,038,345 | 7/1977 | O'Sullivan et al. .................... 260/881 |
| 4,379,863 | 4/1983 | Snyder ................................. 523/105 |
| 4,444,933 | 4/1984 | Columbus et al. ....................... 524/292 |
| 4,542,012 | 9/1985 | Dell ..................................... 424/28 |
| 4,584,192 | 4/1986 | Dell et al. ............................ 424/81 |
| 4,650,826 | 3/1987 | Waniczek et al. ..................... 524/730 |
| 4,958,748 | 9/1990 | Otake ................................ 222/131 |
| 5,045,601 | 9/1991 | Capelli et al. ........................ 525/321 |
| 5,254,132 | 10/1993 | Barley et al. ......................... 606/214 |
| 5,306,490 | 4/1994 | Barley ............................... 424/78.35 |
| 5,328,687 | 7/1994 | Leung ............................... 424/78.35 |
| 5,480,935 | 1/1996 | Greff et al. ........................... 524/776 |
| 5,580,565 | 12/1996 | Tighe et al. .......................... 424/400 |
| 5,653,769 | 8/1997 | Barley et al. ........................... 623/66 |
| 5,684,042 | 11/1997 | Greff et al. ............................ 514/527 |
| 5,730,994 | 3/1998 | Askill et al. ............................ 424/402 |
| 5,753,699 | 5/1998 | Greff et al. ............................ 514/527 |

FOREIGN PATENT DOCUMENTS

WO 93/25196  12/1993  WIPO.

OTHER PUBLICATIONS

Masterson, M.D., "Skin Preparation", Chapter 9, in *Surgical Infections, Diagnosis and Treatment*, Meakins, Ed., Scientific American, Inc., New York, USA, Publisher, pp. 119–125 (1994).

Osuna, et al., "Comparison of an Antimicrobiol Adhesive Drape and Povidone–Iodine Preoperative Skin Preparation in Dogs", Veterinary Surgery, 21(6):458–462 (1992).

Hagen, et al., "Comparison of Two Skin Preps Used in Cardiac Surgical Prodecures", AORN Journal, 62(3):393–402 (1995).

Alexander, et al., "Development of a Safe and Effective One–Minute Preoperative Skin Preparation", Arch. Surg., 120:1357–1361 (1985).

Chiu, et al., "Plastic Adhesive Drapes and Wound Infection After Hip Fracture Surgery", Aust. N.Z. J. Surg., 63:798–801 (1993).

Ritter, et al., "Retrospective Evaluation of an Iodophor–Incorporated Antimicrobiol Plastic Adhesive Wound Drape", Clinical Orthopedics and Related Research, pp. 307–308 (1988).

Duhaime, et al., "Distribution of Bacteria in the Operating Room Environment and its Relation to Ventricular Shunt Infections: a Prospective Study", Child's Verv. Syst., 7:211–214 (1991).

*Primary Examiner*—Kimberly Jordan
*Attorney, Agent, or Firm*—Burns, Doane, Swecker & Mathis, LLP

[57] ABSTRACT

Disclosed are methods for the application of a cyanoacrylate/anti-microbial composition over mammalian skin surfaces to peri-wound and peri-mucosal areas. The composition can also be applied over medicament that has been applied onto the skin surface.

14 Claims, No Drawings

APPLICATION OF CYANOACRYLATE/ANTI-MICROBIAL COMPOSITIONS TO THE PERI-WOUND OR PERI-MUCOSAL AREA

BACKGROUND OF THE INVENTION

Field of the Invention

This invention is directed to the use of cyanoacrylate/PVP-iodine compositions for the treatment of the peri-wound or peri-mucosal skin. Specifically, the methods of this invention involve the application of a cyanoacrylate/PVP-iodine composition over mammalian skin surfaces peripheral to and surrounding a wound or a mucosal area such as a stoma. The composition can be applied to form a protective barrier layer on skin that is exposed to urine or fecal waste. The composition can also be applied over medicament that has been applied onto the skin surface. The cyanoacrylate composition to be used can be stored in dispensers for single or repeated/intermittent use and can be applied to the skin by spraying, painting etc. of the composition.

References

The following publications, patent applications and patents are cited in this application as superscript numbers:

[1] Masterson, M. D., "Skin Preparation", Chapter 9, in Surgical Infections, Diagnosis and Treatment, Meakins, Ed., Scientific American, Inc., New York, USA, Publisher, pp. 119–125 (1994)

[2] Osuna, et al., "Comparison of an Antimicrobial Adhesive Drape and Povidone-Iodine Preoperative Skin Preparation in Dogs", Veterinary Surgery, 21(6):458–462 (1992)

[3] Hagen, et al., "A Comparison of Two Skin Preps Used in Cardiac Surgical Procedures", AORN Journal, 62(3):393–402 (1995)

[4] Alexander, et al., "Development of a Safe and Effective One-Minute Preoperative Skin Preparation", Arch. Surg., 120:1357–1361 (1985)

[5] Chiu, et al., "Plastic Adhesive Drapes and Wound Infection After Hip Fracture Surgery", Aust. N. Z. J. Surg., 63:798–801 (1993)

[6] Barley, "Methods for Retarding Blister Formation by Use of Cyanoacrylate Adhesives", U.S. Pat. No. 5,306,490, issued Apr. 26, 1994.

[7] Barley, et al., Methods for Treating Suturable Wounds by Use of Sutures and Cyanoacrylate Adhesives, U.S. Pat. No. 5,254,132, issued Oct. 19, 1993

[8] McIntire, et al., U.S. Pat. No. 3,654,239, for Process for the Preparation of Poly(α-Cyanoacrylates), issued Apr. 4, 1972

[9] Barley, et al., International Patent Application Publication No. WO 93/25196, for Methods for Treating Non-Suturable Wounds by Use of Cyanoacrylate Adhesives, published Dec. 23, 1993

[10] Barley, et al., U.S. Pat. No. 5,653,789, for Methods for Reducing Skin Irritation From Artificial Devices by Use of Cyanoacrylate Adhesives, issued Aug. 5, 1997

[11] Ritter, et al., "Retrospective Evaluation of an Iodophor-Incorporated Antimicrobial Plastic Adhesive Wound Drape", Clinical Orthopedics and Related Research, pp. 307–308 (1988)

[12] Duhaime, et al., "Distribution of Bacteria in the Operating Room Environment and its Relation to Ventricular Shunt Infections: a Prospective Study", Child's Verv. Syst., 7:211–214 (1991)

[13] O'Sullivan, et al., U.S. Pat. No. 4,038,345, for High Viscosity Cyanoacrylate Adhesive Compositions, and Process for Their Preparation, issued Jul. 26, 1977

[14] Robertson, U.S. Pat. No. 3,722,599 for Fluorocyanoacrylates issued Mar. 27, 1973

[15] Leung, U.S. Pat. No. 5,328,687 for Biocompatible Monomer and Polymer Compositions, issued Jul. 12, 1994

[16] Askill et al., U.S. patent application Ser. No. 08/781,279, for Methods for Draping Surgical Incision Sites filed Jan. 10, 1997 for now U.S. Pat. No. 5,730,994, issued Mar. 24, 1998; and

[17] U.S. patent application Ser. No. 08/912,678, for Methods for Draping Surgical Incision Sites filed Aug. 18, 1997 now U.S. Pat. No. 5,807,563, issued Sep. 15, 1998

[18] Greff et al., U.S. Pat. No. 5,480,935, for Cyanoacrylate Adhesive Compositions issued on Jan. 2, 1996

[19] Greff, et al., U.S. patent application Ser. No. 08/781,409 for Cyanoacrylate Compositions Comprising an Antimicrobial Agent to issue as U.S. Pat. No. 5,684,042 on Nov. 4, 1997

[20] Snyder, U.S. Pat. No. 4,379,863 for Copolymer Composition and Delivery System for Providing a Protective Barrier Film for the Skin issued Apr. 12, 1983

All of the above publications, patent applications and patents are herein incorporated by reference in their entirety to the same extent as if each individual publication, patent application or patent was specifically and individually indicated to be incorporated by reference in its entirety.

State of the Art

Known medical uses of cyanoacrylate polymers are as alternatives or adjuncts to sutures[7] or as a hemostat[8]. Other described uses of cyanoacrylate polymers include their use to prevent friction blister formation[6], treat small non-suturable wounds[9], and inhibit surface skin irritation arising from friction between the skin surface and artificial devices such as tapes, prosthetic devices, casts, and the like.[10]

In contrast to the methods of this invention, Snyder[20] describes the use of a composition to form a protective barrier film on skin. The composition comprises polymerized materials in the form of acrylate resins that are applied to the skin; the protective barrier film is formed upon evaporation of the solvent. The protective barrier so formed, however, has a variety of deficiencies associated with the use of prepolymerized films including weak adherence of the film to the skin resulting in premature peeling of the film.

This invention is directed to the discovery that cyanoacrylates can be used to form in situ a barrier layer or coating over intact skin adjacent to a wound or stoma to prevent further injury to the intact skin and to provide a source of anti-microbial agent to the skin.

SUMMARY OF THE INVENTION

This invention is directed to use of cyanoacrylate/PVP-iodine compositions in the treatment of peri-wounds and peri-mucosal skin. Specifically, the methods of this invention involve the application of a cyanoacrylate/PVP-iodine composition over mammalian peri-wound or peri-mucosal skin surfaces.

In situ polymerization of the cyanoacrylate composition provides for an adherent polymeric film on the skin peripheral to the wound or stoma which acts to control additional tearing of the skin and to provide an anti-microbial benefit to the peri-wound or peri-mucosal skin. The adherence of the polymeric film to the skin surface is so strong that the possibility of lifting of the film is effectively removed. Additionally, the cyanoacrylate composition can be applied as a liquid/gel to the skin surface which permits formation of an adherent film over any skin contour including elbows, knees, hips, and the like.

Since the polymeric film is naturally shed from the skin surface 1–4 days after application, there is no need to effect removal of the film after the wound has healed. This polymeric film forms an anti-microbial barrier to external sources of wound or stoma contamination. Over time the iodine will be released from the resulting film thereby providing for peri-wound or peri-stoma infection protection not now available.

Accordingly, in one of its method aspects, this invention is directed to a method for treating peri-wound or peri-mucosal skin by forming an adherent, surface conforming cyanoacrylate film around a wound or stoma of a patient which method comprises:

(a) defining a wound or stoma on the patient;

(b) applying a sufficient amount of a composition comprising a polymerizable cyanoacrylate ester and PVP-iodine onto the skin surface of the patient peripheral to the wound or stoma defined in (a) above so as to peripherally surround this site with the composition;

(c) polymerizing the cyanoacrylate ester so as to form a flexible, waterproof, polymer layer which adheres to the area(s) where the composition was applied.

Preferably, the polymerizable cyanoacrylate ester comprises a cyanoacrylate ester which, in monomeric form, is represented by formula I:

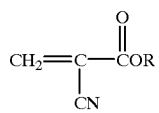

I where R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

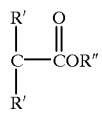

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula I, R is alkyl of from 2 to 10 carbon atoms and more preferably alkyl of from 4 to 10 carbon atoms. Even more preferably, R is butyl, pentyl, octyl, decyl or mixtures thereof and most preferably, R is n-butyl.

Antimicrobial agents would include antibacterials, antifungals, antibiotics, anti-virals and anti-parasitics. Preferably the antimicrobial agent is a complex of iodine molecules with a biocompatible polymer, more preferably, the antimicrobial agent is polyvinylpyrrolidinone polymer complexed with iodine.

The antimicrobial cyanoacrylate compositions may further comprise an effective amount of a polymerization inhibitor and a biocompatible plasticizer.

Application of the layer of cyanoacrylate composition is preferably made onto the surface of intact or uninjured skin. More preferably, the skin is further characterized as lacking any infection, open wounds, etc. which would permit the polymer to penetrate from the surface of the epidermis to or beyond the dermal layer. However, the location of the cyanoacrylate composition will be peripheral to and surround an infection, open wound or stoma.

In another preferred embodiment, the polymerized cyanoacrylate composition has a thickness of no more than about 1 millimeter and, more preferably, the polymer layer has a thickness of from about 2 to about 500 microns and still more preferably from about 20 to about 100 microns.

DETAILED DESCRIPTION OF THE PREFERRED EMBODIMENTS

This invention is directed to the use of cyanoacrylate/PVP-iodine compositions for the treatment of the peri-wound or peri-mucosal skin. Specifically, the methods of this invention involve the application of a cyanoacrylate/PVP-iodine composition over mammalian skin surfaces peripheral to and surrounding a wound or stoma. The composition can also be applied over medicament that has been applied onto the skin surface. The cyanoacrylate composition to be used can be stored in dispensers for single or repeated/intermittent use and can be applied to the skin by spraying, painting etc. of the composition. However, prior to discussing this invention in further detail, the following terms will first be defined.

Definitions

As used herein, the following terms have the following meanings:

The term "wound" refers to any wound or injury, including surgically created wounds and accidental or traumatic wounds which have broken the dermal layer, such as stoma sites, tracheostomies, sites of catheter punctures, skin ulcers which have broken the skin and contaminated or infected wounds where the wound will not be closed by surgical means.

The term "peripheral to the wound" or "peri-wound area" or peri-mucosal area" refers to the area adjacent to the wound or stoma. This area typically extends from immediately adjacent the wound or stoma up to about 30 cm and preferably from about 3 cm to about 30 cm from the wound or stoma. It being understood that the inner boundary of the area peripheral to the wound may conform to or parallel the shape of the wound.

The term "polymerizable cyanoacrylate esters" refers to polymerizable formulations comprising cyanoacrylate monomers or polymerizable oligomers which, in their monomeric form, are preferably compounds represented by formula I as described above.

More preferably, in formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, octyl or decyl and most preferably, R is n-butyl. Mixtures of such compounds can also be employed.

A preferred cyanoacrylate ester for use in the invention is n-butyl-2-cyanoacrylate.

The polymerizable cyanoacrylate esters described herein rapidly polymerize in the presence of water vapor or tissue protein, and the cyanoacrylate bonds to human skin tissue without causing histotoxicity or cytotoxicity.

Such polymerizable cyanoacrylate esters are sometimes referred to herein as prepolymers and composition formulations comprising such esters are sometimes referred to herein as prepolymer compositions.

These polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

The term "biocompatible plasticizer" refers to any material which is soluble or dispersible in the cyanoacrylate composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (~20 weight percent or less), acetyl trihexyl citrate (~20 weight percent or less) butyl benzyl phthalate, dibutyl phthalate, dioctylphthalate, n-butyryl tri-n-hexyl citrate, diethylene glycol dibenzoate (~20 weight percent or less) and the like. The particular biocompatible plasticizer employed is not critical and preferred plasticizers include dioctyl phthalate, and $C_2$–$C_4$-acyl tri-n-alkyl ($C_1$–$C_6$) citrates.

The term "polymerization inhibitor" refers to any material which is soluble or dispersible in the cyanoacrylate composition and which, in the amounts employed, inhibits the premature polymerization of the composition and is compatible with the skin. Suitable polymerization inhibitors are well known in the art and include 4-methoxyphenol (50 to 1000 ppm based on weight of composition absent any antimicrobial agent) and sulfur dioxide (50 to 1000 ppm based on weight of composition absent any antimicrobial agent). Other preferred polymerization inhibitors include glacial acetic acid, free radical inhibitors (e.g. hydroquinones) and the like which can be used alone or in combination with 4-methoxyphenol and/or $SO_2$.

The term "antimicrobial agent" refers to an agent which destroys microbes (i.e., bacteria, fungi, parasites, yeasts and viruses) thereby preventing their development and their pathogenic action. A particularly preferred antimicrobial agent is a complex of iodine molecules with a biocompatible polymer, more preferably the antimicrobial agent is polyvinylpyrrolidinone polymer complexed with iodine.

Methods

An antimicrobial agent may be applied to the area surrounding the cleaned wound and/or the stoma. The antimicrobial agent can be any suitable agent including iodine based solutions, alcohols, etc. In one embodiment, an iodine prep solution is applied to the area peripheral to the cleaned wound.

Then an adherent polymeric cyanoacrylate film is formed peripheral to the wound or stoma by applying a cyanoacrylate ester composition to the intact skin surface peripheral to the wound or stoma. As noted above, this composition comprises polymerizable cyanoacrylate monomers and/or reactive oligomers which, upon contact with the surface skin moisture, tissue protein, etc. polymerizes in situ to form a cyanoacrylate polymer film.

Polymerization occurs at ambient skin temperature while maintaining the skin surface under suitable conditions to allow polymerization to proceed. In general, the particular length of time required for polymerization will vary depending on factors such as the amount of composition applied, the temperature of the skin, the moisture content of the skin, the surface area of skin to which the composition was applied, and the like. However, in a preferred embodiment, polymerization is generally complete within about 10 to about 100 seconds while the skin is maintained at ambient conditions. During this period, the patient is maintained in a position which permits the cyanoacrylate to polymerize and form a polymeric peripheral film while minimizing any patient movement which might dislodge the cyanoacrylate from the peri-wound or peri-mucosal area or create undesirable bonding.

Sufficient amounts of the composition are employed to cover (i.e., coat) the area peripheral to the wound or stoma with a layer of the cyanoacrylate polymer. If necessary, excess cyanoacrylate monomer can be removed from the skin with a wipe or tissue paper before polymerization or, after polymerization, any polymer formed at unintended sites can be removed with acetone (nail polish remover).

After polymerization, the resulting polymeric film strongly adheres to the skin, is flexible and waterproof. Such strong adherence effectively eliminates the possibility that the film will separate from the patient's skin. However, notwithstanding such strong adherence, the polymeric film will only adhere to the skin for a period of about 1–4 days after which time it sloughs off. This occurs because the cyanoacrylate polymer adheres only to the uppermost portion of the epidermal layer which is continuously in the process of being sloughed off and replaced by the underlying cells.

The polymeric film should be maintained in a unbroken manner surrounding and peripheral to the wound or stoma. This can be assured by careful application of the cyanoacrylate composition onto the skin. Additionally, the use of a plasticizer in the composition will facilitate the maintenance of the polymeric film in an unbroken manner and will inhibit cracking of the film.

In one preferred embodiment, after application of the initial polymeric layer, a second, preferably thinner, layer is applied thereto. Additional amounts of cyanoacrylate composition can be applied as needed to maintain an unbroken coating over the surface skin areas.

Application is conducted under conditions wherein the polymeric film has a thickness of no more than about 1 millimeter and, more preferably, the polymer layer has a thickness of from about 2 to about 500 microns and still more preferably from about 20 to about 100 microns. If thinner polymeric film is desired, then the polymeric film should have a thickness of from about 2 to about 50 microns and preferably from 10 to 40 microns. One drop of the cyanoacrylate composition can cover from about 5 $cm^2$ to about 25 $cm^2$ area. The amount of cyanoacrylate composition applied to a unit area of skin to obtain such thicknesses is well within the skill of the art.

The size and thickness of the polymeric film formed onto the skin surface area can be readily controlled by the amount and viscosity of cyanoacrylate ester composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is one example of a dispenser which dispenses the cyanoacrylate composition in a controlled dropwise manner. Other methods for the controlled dispersement of the cyanoacrylate composition include, by way of example, a spray applicator, brush, wipe, swab or solid paddle applicator, applicators for repeated and intermittent use of the cyanoacrylate composition and the like.

In applicators, the cyanoacrylate composition is stored at ambient conditions. The cyanoacrylate composition may be provided as a sterile liquid or may be sterilized if needed.

After polymerization, the cyanoacrylate film has biostatic and anti-microbial properties. The peripheral cyanoacrylate film, by strongly adhering to the skin, impedes or prevents the migration of bacteria and other microbes from the area peripheral to the wound into the wound or stoma It also aids in wound management and maintaining the cleanliness of the wound. In one particularly preferred embodiment, the cyanoacrylate composition further comprises a compatible antimicrobial agent to provide antimicrobial properties to the composition.

In addition, after polymerization the cyanoacrylate film shields the skin from discharge from the ostomy. In the case of stomas, the adhesive holding the ostomy equipment to the patient can be applied directly to the polymerized cyanoacrylate film. Therefore, an additional benefit is that the cyanoacrylate film can protect the patient from the adhesives used.

Finally, after polymerization the cyanoacrylate film also acts to strengthen the skin to prevent tearing of the skin at the edges of the wound or stoma.

Compositions

The cyanoacrylate compositions comprising the polymerizable cyanoacrylate esters are prepared by conventional methods of mixing the appropriate components until homogenous.

The specific viscosity of these compositions depends, in part, on the intended application of the composition. For example, relatively low viscosities are often preferred where application is to be made to a large surface area (e.g., abdominal surfaces). This preference results from the fact that those forms are less viscous and, accordingly, will permit more facile large surface area application of a thin layer. Contrarily, where application is to be made to a specific position on the skin (e.g., elbow surfaces), higher viscosity compositions, including those containing thiotropic materials, are preferred to prevent "running" of the material to unintended locations.

Accordingly, these compositions have a viscosity of from about 2 to 50,000 centipoise at 20° C. Preferably the less viscous compositions have a viscosity of from about 2 to 1,500 centipoise at 20° C. More preferably, the cyanoacrylate composition is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like with PMMA being preferred. Fumed silica is particularly useful in producing a gel for topical application having a viscosity of from about 1500 to 50,000 centipoise at 20° C. Suitable thickening agents for the compositions described herein also include a partial polymer of the alkyl cyanoacrylate as disclosed in U.S. Pat. Nos. 3,654,239[8] and 4,038,345[13] both of which are incorporated herein by reference in their entirety.

Thickening agents are deemed to be biocompatible if they are soluble or dispersible in the composition and are compatible with the skin as measured by the lack of moderate to severe skin irritation.

The cyanoacrylate compositions preferably include a biocompatible plasticizer and such plasticizers are preferably included in the composition at from about 10 to 30 weight percent and more preferably at from about 18 to 25 weight percent based on the total weight of the composition absent any antimicrobial agent.

Additionally, the cyanoacrylate compositions described herein preferably include a polymerization inhibitor in an effective amount to inhibit premature polymerization of the composition. In one embodiment, the inhibitor is sulfur dioxide which is employed at from about 50 to 1000 ppm, preferably from 100 to 500 ppm, based on the total weight of the composition absent any antimicrobial agent. In another preferred embodiment, the inhibitor is 4-methoxyphenol which is employed at from about 50 to 500 ppm, preferably from 100 to 500 ppm, based on the total weight of the composition absent any antimicrobial agent. In a particularly preferred embodiment where the cyanoacrylate composition additionally comprises povidone-iodine, the inhibitor is 4-methoxyphenol which is employed at from about 50 to 500 ppm and sulfur dioxide which is employed at 50 to 500 ppm, each based on the total weight of the composition absent any antimicrobial agent.

The polymerizable cyanoacrylate ester compositions may additionally contain one or more optional additives such as colorants, perfumes, rubber modifiers, modifying agents, etc. In practice, each of these optional additives should be both miscible and compatible with the cyanoacrylate composition and the resulting polymer. Compatible additives are those that do not prevent the use of the cyanoacrylates in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. The amount of each of these optional additives employed in the composition is an amount necessary to achieve the desired effect.

Preferred cyanoacrylate compositions useful in the practice of this invention are also disclosed by Greff, et al., U.S. Pat. No. 5,480,935[18], which patent is incorporated herein by reference in its entirety.

The cyanoacrylate ester composition may further comprise an antimicrobially effective amount of a compatible antimicrobial agent. Such compositions preferably comprise from about 1 to about 40 and preferably 5 to 30 weight percent of the compatible antimicrobial agent either as a solution or as a suspension based on the total weight of the composition. Compatible antimicrobial agents are those which are either soluble or suspendable in the cyanoacrylate composition, which do not cause premature polymerization or prevent polymerization of the cyanoacrylate composition when applied to mammalian skin, and which are compatible with the intended use including biocompatibility with the patient's skin.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidinone polymer which, when complexed with iodine, is also referred to under the common name of povidone-iodine available from BASF, Mt. Olive, N.J., USA. When povidone-iodine is employed in the cyanoacrylate composition, it is preferably from about 5 to about 40 weight percent and more preferably from about 10 to 25 weight percent is added to the cyanoacrylate composition based on the total weight of the composition.

Cyanoacrylate compositions comprising, for example, povidone-iodine are described by Greff, et al., U.S. Pat. No. 5,684,042[19] which patent is incorporated herein by reference in its entirety.

Other suitable antimicrobial agents include complexes of iodine molecules with copolymers of vinylpyrrolidinone and vinyl acetate, copolymers of vinylpyrrolidinone and vinyl acetate cross-linked with polyisocyanates, copolymers of vinylpyrrolidinone and vinyl functionalities, polymers of pyrrolidone and the like. Preferably, however, the iodine containing polymer is povidone iodine which is commercially available from a number of sources.

The use of a compatible antimicrobial agent in the composition permits the agent to be released from the polymeric film thereby reducing microbial growth under the film. Additionally, the compatible antimicrobial agent in the composition migrates from the film toward the wound or stoma, thereby reducing microbial contamination at the wound or stoma. Since the film is maintained peripheral to the wound or stoma for 1–4 days after application of the film, the release of antimicrobial agent further provides post-application anti-infection benefits. In the case of stomas, the antimicrobial agent further provides anti-infection benefits to the peri-mucosal skin which is susceptible to infection due to contamination of the peri-mucosal skin with discharge from the stoma.

Utility

The methods described herein are useful for treating peri-wound or peri-mucosal skin by forming a polymeric film peripheral to and surrounding the wound or stoma of a mammalian patient. The polymeric film finds particular utility in inhibiting microbial contamination of the wound, the peri-wound and peri-mucosal area. Such mammalian patients preferably include humans as well as domestic animals such as horses, cows, dogs, sheep, cats, etc.

The following examples illustrate certain embodiments of the invention but are not meant to limit the scope of the claims in any way.

In the examples below, all temperatures are in degrees celsius (unless otherwise indicated) and all percents are weight percent (also unless otherwise indicated) except for percent inhibition which is true mathematical percentage. Additionally, the following abbreviations have the following meanings. If an abbreviation is not defined, it has its generally accepted meaning.

CFU=colony forming units
ml=milliliters
mm=millimeters
ppm=parts per million
PVP-$I_2$=polyvinylpyrrolidone iodine complex
SAB-DEX=Sabouraud Dextrose
TSA=trypticase soy agar

EXAMPLE 1

The following example was conducted to ascertain the antimicrobial effect of a cyanoacrylate polymer film comprising PVP-iodine.

A. Preparation of the Inoculum

Specifically, the surfaces of two TSA plates, 100×15 mm, were inoculated with stock cultures (maintained on TSA slants) with the following microorganisms using a sterile inoculating loop: *Staphylococcus aureus* (ATCC No. 6538) and *Staphylococcus epidermidis* (ATCC No. 12228). The plates were incubated at 30° to 35° C. for 24 hours. The surfaces of two SAB-DEX agar plates were streaked with *Candida albicans* and incubated at 20–25° C. for 48 hours.

The cultures were harvested with sterile saline. Each culture suspension was collected in a sterile container and sufficient sterile saline was added to reduce the microbial count to obtain a working suspension of approximately $1 \times 10^8$ CFU's per ml.

The specific microorganisms recited above were selected for inclusion herein because they are common human skin pathogens (bacteria and fungus).

B. Inoculation of Plates

Each of the three test microorganisms was used to inoculate individual TSA plates by streaking them with sterile cotton tip applicators saturated with the appropriate suspension. The plates were allowed to dry.

C. Inhibition Study

Films of polymerized n-butyl cyanoacrylate comprising 0%, 10%, 15%, 20% or 30% iodine polyvinylpyrrolidone complex were formed on 25 mm glass fiber filter disks by addition of the corresponding prepolymerized cyanoacrylate composition to the disks and subsequent polymerization in situ. The films were then cut into approximately 11 to 13 $mm^2$ pieces. The pieces were placed in the center of the appropriate inoculated TSA plates. An untreated filter disk was cut into half, and one-half was placed in the center of the appropriate inoculated TSA plate and the other one-half was place in the center of non-inoculated TSA plates, to serve as a negative control. Two inoculated plates of each microorganism were also used as positive controls without the test article. These plates were then incubated for 3 days at 30° to 35° C. After incubation, the plates were removed and examined for any signs of microbial growth inhibition.

The results of this analysis are set forth in Tables I–III below. The sample sizes reported are the portion of the sample actually in contact with the agar. The sizes of the zone of inhibition include the diameters of the entire zone including the test article size.

TABLE I

Results for *Staphylococcus aureus*

| SAMPLE: n-butyl cyanoacrylate comprising | SAMPLE SIZE[1] (in mm) | ZONE OF INHIBITION[1] (in mm) |
| --- | --- | --- |
| 0% PVP-$I_2$ | 12 | 12 |
| 10% PVP-$I_2$ | 12 | 15 |
| 15% PVP-$I_2$ | 12.5 | 14 |
| 20% PVP-$I_2$ | 11.5 | 15.5 |
| 30% PVP-$I_2$ | 12.5 | 20 |
| Untreated Filter Disk | 13[2] | 13[2] |
| Negative Control | 13[2] | 13[2] |
| Positive Control | n/a | 0 |

TABLE II

Results for *Staphylococcus epidermis*

| SAMPLE: n-butyl cyanoacrylate comprising | SAMPLE SIZE[1] (in mm) | ZONE OF INHIBITION[1] (in mm) |
|---|---|---|
| 0% PVP-$I_2$ | 12 | 12 |
| 10% PVP-$I_2$ | 12.5 | 15 |
| 15% PVP-$I_2$ | 12 | 15.5 |
| 20% PVP-$I_2$ | 12.5 | 20.5 |
| 30% PVP-$I_2$ | 13 | 27.5 |
| Untreated Filter Disk | 13[2] | 13[2] |
| Negative Control | 13[2] | 13[2] |
| Positive Control | n/a | 0 |

TABLE III

Results for *Candida albicans*

| SAMPLE: n-butyl cyanoacrylate comprising | SAMPLE SIZE[1] (in mm) | ZONE OF INHIBITION[1] (in mm) |
|---|---|---|
| 0% PVP-$I_2$ | 12 | 12 |
| 10% PVP-$I_2$ | 12.5 | 18.5 |
| 15% PVP-$I_2$ | 12.5 | 23 |
| 20% PVP-$I_2$ | 12.5 | 20.5 |
| 30% PVP-$I_2$ | 13 | 29.5 |
| Untreated Filter Disk | 13[2] | 13[2] |
| Negative Control | 13[2] | 13[2] |
| Positive Control | n/a | 0 |

[1]average of two runs
[2]single run only

The above data demonstrates that the compositions of this invention produce a polymeric cyanoacrylate film which have a broad spectrum of antimicrobial activity. Based on these results, it is expected that these compositions would be antimicrobial when formed in situ on mammalian skin surfaces.

EXAMPLE 2

This example illustrates how application of the cyanoacrylate composition of this invention can be used to treat the peri-wound area.

Specifically, an adult male diagnosed with a decubitus ulcer on the right hip is scheduled for treatment. The ulcer is a stage III open ulcer which is approximately 2×3 cm in size. The ulcer is treated using the standard protocol for ulcers of this type, including washing the ulcer, debriding the ulcer and packing the ulcer.

A viscous antimicrobial composition comprising 58% by weight butyl cyanoacrylate, 5% by weight polymethylmethacrylate, 17% by weight acetyl tri-n-butyl citrate, 20% povidone iodine, 100 parts per million glacial acetic acid, 250 parts per million 4-methoxyphenol and 100 parts per million sulfur dioxide (each based on the total weight of the composition) is applied peripherally to the wound area. The composition is applied as a band about 5 cm wide and about 1 cm away from the wound. The composition is allowed to thoroughly cure (~100 seconds) whereupon a coherent, durable and flexible film is formed over the applied area. This cycle is repeated every two days until the ulcer has completely healed.

From the foregoing description, various modifications and changes in the composition and method will occur to those skilled in the art. All such modifications coming within the scope of the appended claims are intended to be included therein.

What is claimed is:

1. A method for treating peri-wound or peri-mucosal skin by forming an adherent, surface conforming cyanoacrylate film around a wound or stoma of a patient which method comprises:

(a) identifying a wound or stoma on the patient;

(b) applying a sufficient amount of a composition comprising a polymerizable cyanoacrylate ester and an antimicrobially effective amount of a compatible antimicrobial agent onto the skin surface of the patient peripheral to the wound or stoma identified in (a) above so as to peripherally surround this site with the composition;

(c) allowing the cyanoacrylate ester to polymerize in situ so as to form a flexible, waterproof, polymer layer which adheres to the area(s) where the composition was applied.

2. The method according to claim 1 wherein the polymerizable cyanoacrylate composition comprises a cyanoacrylate ester which, in monomeric form, is represented by formula I:

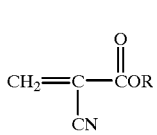

where R is selected from the group consisting of:
   alkyl of 1 to 10 carbon atoms,
   alkenyl of 2 to 10 carbon atoms,
   cycloalkyl groups of from 5 to 8 carbon atoms,
   phenyl,
   2-ethoxyethyl,
   3-methoxybutyl,
   and a substituent of the formula:

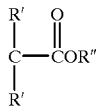

wherein each R' is independently selected from the group consisting of:
   hydrogen and methyl, and
   R" is selected from the group consisting of:
      alkyl of from 1 to 6 carbon atoms,
      alkenyl of from 2 to 6 carbon atoms,
      alkynyl of from 2 to 6 carbon atoms,
      cycloalkyl of from 3 to 8 carbon atoms,
      aralkyl selected from the group consisting of benzyl, methylbenzyl and phenylethyl,
      phenyl, and
      phenyl substituted with 1 to 3 substituents selected from the group consisting of hydroxy, chloro, bromo, nitro, alkyl of 1 to 4 carbon atoms, and alkoxy of from 1 to 4 carbon atoms.

3. The method according to claim 2 wherein R is alkyl of from 2 to 10 carbon atoms.

4. The method according to claim 3 wherein R is alkyl of from 4 to 10 carbon atoms.

5. The method according to claim 4 wherein R is selected from the group consisting of butyl, octyl or decyl.

6. The method according to claim 5 wherein R is n-butyl.

7. The method according to claim 1 wherein the compatible antimicrobial agent is polyvinylpyrrolidinone iodine.

8. The method according to claim 1 wherein said cyanoacrylate composition further comprises a biocompatible plasticizer.

9. The method according to claim 8 wherein said biocompatible plasticizer is dioctyl phthalate.

10. The method according to claim 1 wherein said cyanoacrylate composition further comprises a polymerization inhibitor.

11. The method according to claim 10 wherein said polymerization inhibitor is sulfur dioxide.

12. The method according to claim 1 wherein the polymer layer has a thickness of no more than about 1 millimeter.

13. A method for treating peri-wound or peri-mucosal skin by forming an adherent, surface conforming cyanoacrylate film on the skin around a wound or stoma of a patient which method comprises:

(a) identifying a wound or stoma on the patient;

(b) applying a sufficient amount of a composition comprising polymerizable cyanoacrylate ester monomers and/or oligomers onto the skin surface of the patient peripheral to the wound or stoma identified in (a) above so as to peripherally surround this site with the composition wherein the polymerizable cyanoacrylate ester, in monomeric form, comprises:

(i) polymerizable n-butyl cyanoacrylate which, in monomeric form, is represented by formula II:

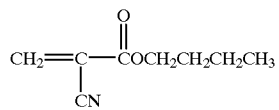

II (ii) from 18 to 25 weight percent of $C_2$–$C_4$ acyl tri-n-alkyl ($C_1$–$C_6$) citrate based on the total weight of the composition absent polyvinylpyrrolidone iodine;

(iii) from 5 to 40 weight percent of polyvinylpyrrolidone iodine based on the total weight of the composition;

(c) allowing the cyanoacrylate ester to polymerize in situ so as to form a flexible, waterproof, polymer layer which adheres to the area(s) where the composition was applied.

14. The method according to claim 13 wherein the polymer layer has a thickness of no more than about 1 millimeter.

* * * * *